United States Patent [19]

Khalil et al.

[11] Patent Number: 4,810,655

[45] Date of Patent: Mar. 7, 1989

[54] METHOD FOR MEASURING OXYGEN CONCENTRATION

[75] Inventors: Gamal-Eddin Khalil, Bellevue; Martin P. Gouterman; Edmond Green, both of Seattle, all of Wash.

[73] Assignee: Abbott Laboratories, North Chicago, Ill.

[21] Appl. No.: 931,746

[22] PCT Filed: Jun. 27, 1986

[86] PCT No.: PCT/US86/01362

§ 371 Date: Sep. 11, 1986

§ 102(e) Date: Sep. 11, 1986

[87] PCT Pub. No.: WO87/00023

PCT Pub. Date: Jan. 15, 1987

Related U.S. Application Data

[63] Continuation-in-part of Ser. No. 752,262, Jul. 3, 1985, abandoned.

[51] Int. Cl.⁴ .................. G01N 21/76; G01N 33/52; A61B 5/00
[52] U.S. Cl. ..................... 436/138; 128/633; 128/634; 128/665; 128/666; 250/459.1; 356/41; 436/136; 436/172; 436/178
[58] Field of Search ............. 436/136, 138, 172, 175, 436/178; 128/633, 634, 664, 665, 666; 250/458.1, 459.1; 356/39, 40, 41

[56] References Cited

U.S. PATENT DOCUMENTS

| Re. 31,832 | 2/1985 | Samulski | 250/459.1 X |
|---|---|---|---|
| 3,429,667 | 2/1969 | Hart et al. | 436/136 X |
| 3,612,866 | 10/1971 | Stevens | 436/136 X |
| 3,725,658 | 4/1973 | Stanley et al. | 436/136 X |
| 4,003,707 | 1/1977 | Lubbers et al. | 436/172 |
| 4,223,226 | 9/1980 | Quick et al. | 250/458.1 |
| 4,245,507 | 1/1981 | Samulski | 374/159 |
| 4,399,099 | 8/1983 | Buckles | 436/136 X |
| 4,476,870 | 10/1984 | Peterson et al. | 128/665 X |
| 4,542,987 | 9/1985 | Hirschfeld | 356/44 |
| 4,652,143 | 3/1987 | Wickersheim et al. | 250/459.1 X |

FOREIGN PATENT DOCUMENTS

| 2538550 | 6/1984 | France . | |
|---|---|---|---|
| 0893853 | 12/1981 | U.S.S.R. | 436/136 |
| 2132348 | 7/1984 | United Kingdom . | |

OTHER PUBLICATIONS

Spellane et al., Inorg. Chem., vol. 19, pp. 386-391, 1980.
Peterson et al., Rev. Sci. Instrum., vol. 51, No. 5, pp. 670-671, 1980, Class 436/172.
Brown, Rev. Sci. Instrum., vol. 34, No. 4, pp. 414-415, 1963, Class 250/459.1.
Stadelmann, Journal of Luminescence, vol. 3, No. 2, pp. 143-151, 1970, Class 250/459.1.
Chernyavskii et al., J. Appl. Spectrosc., vol. 13, No. 5, pp. 1471-1474, 1970, Class 250/459.1.
Aartsma et al., J. Am. Chem. Soc., vol. 104, No. 23, pp. 6278-6283, 1982.
Vogler et al., Inorganic Chimica Acta, vol. 46, pp. 101-105, 1980.
Eastwood et al., J. Mol. Spectroscopy, vol. 35, No. 3, pp. 359-375, 1970.
Callis et al., J. Mol. Spectroscopy, vol. 39, No. 3, pp. 410-420, 1971.
Gouterman et al., J. Am. Chem. Soc., vol. 97, pp. 3142-3149, 1975.
Callis et al., J. Phys. Chem., vol. 77, No. 2, pp. 154-157, 1972.
Gouterman, "Optical Spectra and Electronic Structure of Porphyrins and Related Rings", Chapter 1, pp. 1-165, in *The Porphyrins*, vol. III, D. Dolphin, Ed., Academic Press, N.Y., 1978.

*Primary Examiner*—Barry S. Richman
*Assistant Examiner*—Robert J. Hill, Jr.
*Attorney, Agent, or Firm*—Christensen, O'Connor, Johnson & Kindness

[57] ABSTRACT

Methods and compositions are described for measuring oxygen concentration, particularly for monitoring oxygen in the blood with a fiber optic catheter. Oxygen concentration is determined by observing quenching of the emission from a luminescent (phosphorescent of fluorescent) molecule embedded in an oxygen-permeable matrix. A test fluid of unknown oxygen concentration is contacted with the matrix containing at least one luminescent substance. The matrix is subjected to irradiation over some period of time by light of a wavelength that is strongly absorbed by the luminescent substance, and a measure of the time dependence of luminescent emission intensity $I(t)$ is obtained. Three modes of determining oxygen concentration from $I(t)$ are described.

33 Claims, 11 Drawing Sheets

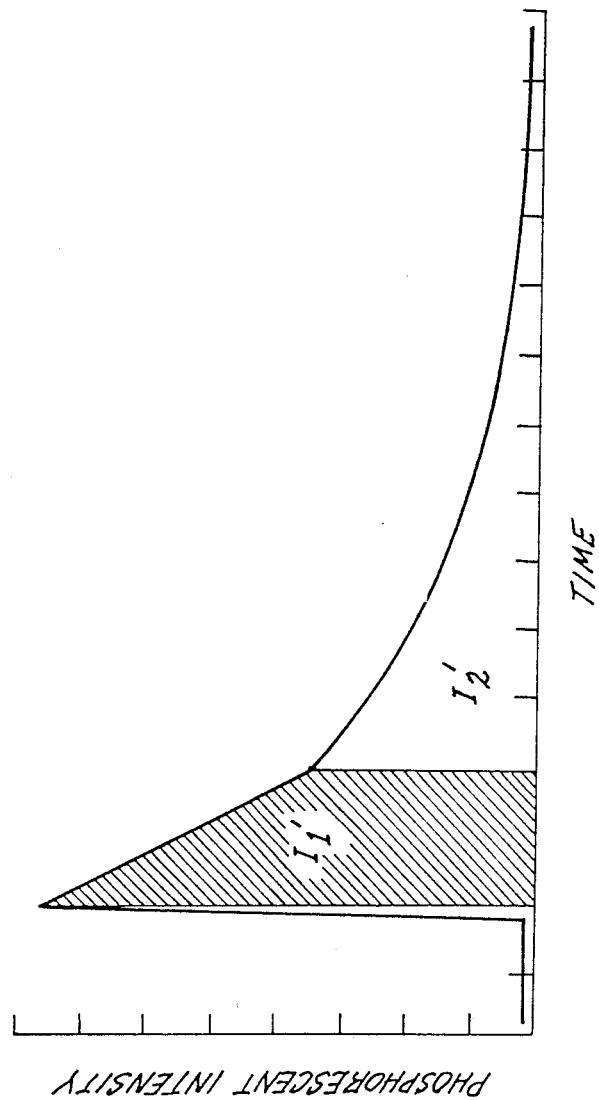

METHOD FOR MEASURING OXYGEN CONCENTRATION

This is a continuation-in-part of our prior application Ser. No. 752,262, filed July 3, 1985 now abandoned, the benefit of the filing date of which is hereby claimed under 35 U.S.C 120.

FIELD OF THE INVENTION

This invention relates generally to the measurement of oxygen concentration using the quenching of emission of a luminescent aromatic molecule embedded in a plastic medium.

BACKGROUND OF THE INVENTION

It is known that a luminescent aromatic molecule embedded in plastic is subject to quenching by oxygen present in the gas or liquid in contact with the plastic. This phenomenon was reported by Bergman (Nature 218:396, 1966), and a study of oxygen diffusion in plastic was reported by Shaw (Trans. Faraday Soc. 63:2181–2189, 1967). Stevens, in U.S. Pat. No. 3,612,866, ratios the luminescence intensities from luminescent materials dispersed in oxygenpermeable and oxygen-impermeable plastic films to determine oxygen concentration. Lubbers et al. in U.S. Pat. No. 4,003,707 proposed the possibility of positioning the emitting substance at the end of an optical fiber. Peterson et al. in U.S. Pat. No. 4,476,870 also employs the quenching of an emitting molecule in plastic at the end of an optical fiber. Both Lubbers and Peterson reference emission against scattered exciting light.

The quenching of the luminescence of an emitter at the end of an optical fiber has been used in temperature sensors. For temperature probes the emitters are generally solid phosphors rather than an aromatic molecule embedded in plastic, since access by molecules from the environment is not desirable. Various methods have been used to measure the amount of quenching: (i) Quick et al. in U.S. Pat. No. 4,223,226 ratios the intensity at one wavelength of the emission against another; (ii) Quick et al. also proposes determining the length of time it takes for the signal to fall from one level to another; (iii) Samulski in U.S. Pat. No. 4,245,507 (reissued as U.S. Pat. No. Re. 31,832) proposes to measure quenching by determining the phase of the emitted life. In a very recent patent for temperature sensing at the end of an optical fiber, Hirschfeld in U.S. Pat. No. 4,542,987 proposes, in addition to method (i), that (iv) emission lifetime be used to measure quenching and that (v) Raman scattered light can be used as a reference.

Eastwood and Gouterman (1970) noted generally with respect to Pd and Pt porphyrin complexes that their "relatively high [emission] yields and short triplet lifetimes . . . may make these systems useful as . . . biological probes for the presence of oxygen." More recently, Bacon and Demas in UK Patent Application No. 2,132,348A propose the use of, inter alia, porphyrin complexes of $VO^{2+}$, $CU^{2+}$, $Pt^{2+}$, $ZN^{2+}$ and $Pd^{2+}$ or dimeric Rh, Pt, or Ir complexes of monitoring oxygen concentration by emission quenching of intensity or lifetime. Suitable ligands would reportedly be etioporphyrin, octaethylporphin, and porphin.

SUMMARY OF THE INVENTION

Methods and compositions are described for measuring oxygen concentration, particularly for monitoring oxygen in the blood with a fiber optic catheter. Oxygen concentration is determined by observing quenching of the emission from a luminescent (phosphorescent or fluorescent) molecule embedded in oxygen-permeable plastic. A test fluid of unknown oxygen concentration is contacted with a plastic film containing at least one luminescent substance. The film is subjected to irradiation over some period of time by light of a wavelength that is strongly absorbed by the luminescent substance, and a measure of the time dependence of luminescent emission intensity I(t) is obtained. Three modes of determining oxygen concentration from I(t) are described. (i) Subsequent to a brief (approximately 5 us) flash of light $I(t_i)$ is determined by use of a transient recorder and fit to Eq. (6). An average decay rate $$\bar{k} = (A_1 K_1 + A_2 k_2)/(A_1 + A_2) \qquad (7)$$

is determined, and $\bar{k}$ used for the Stern-Volmer plot of Eq. (1). (ii) The period of linear decay of luminescent emission is determined from the I(t) data, and that intensity versus time profile is referenced against similarly obtained profiles for reference fluids of known oxygen concentration, using slopes, intensity or time setpoints. (iii) The sample is irradiated for some time interval (generally under 50 us) using a flash lamp or a light emitted diode. Intensity segments of emission, $I_1$ and $I_2$, are determined during two time intervals defined with respect to the time of irradiation. These two intensity segments are compared to form a ratio R, and a calibration plot of R versus oxygen pressure is obtained using solutions of known oxygen concentration. Three different methods for determining $I_1$, $I_2$, and R are presented. These methods (i–iii) of measuring quenching are insensitive to variation in plastic thickness and emitter concentration of the probe and to decomposition during operation. Methods (i–iii) also take into account the non-exponential decay of the emission, and thus extend the pressure range over which the probe is sensitive. Method (iii) requires at most one point calibration against atmospheric oxygen.

Also disclosed are photostable luminescent molecules for use with the subject method. In a preferred embodiment platinum tetra(pentafluorophenyl)porphyrin, Pt(TFPP), serves as the luminescent oxygen quenching-sensitive molecule. Pt(TFPP) has a strong absorbance in the visible region, a strong phosphorescence with lifetime of roughly 100 μs, and is photostable. Photostability is provided by the substitution of fluorine atoms in the periphery of the synthetic porphyrin ring. Other suitable fluorinated luminescent molecules include metallo derivatives, particularly platinum and palladium derivatives, of partially or fully fluorinated octaephylporphyrin, tetraphenylporphyrin, tetrabenzoporphyrin, or the chlorins, bacteriochlorins, or isobacteriochlorins thereof. The latter reduced porphyrins have the advantage that their absorption is red-shifted to a region for which light emitting diodes can be used for excitation.

BRIEF DESCRIPTION OF THE DRAWINGS

FIG. 7 is a representative plot showing the two intensity segments $I_1'$ and $I_2'$ as used in Equation (10) in conjunction with system 10';

DETAILED DESCRIPTION OF THE PREFERRED EMBODIMENT

Figure 1:
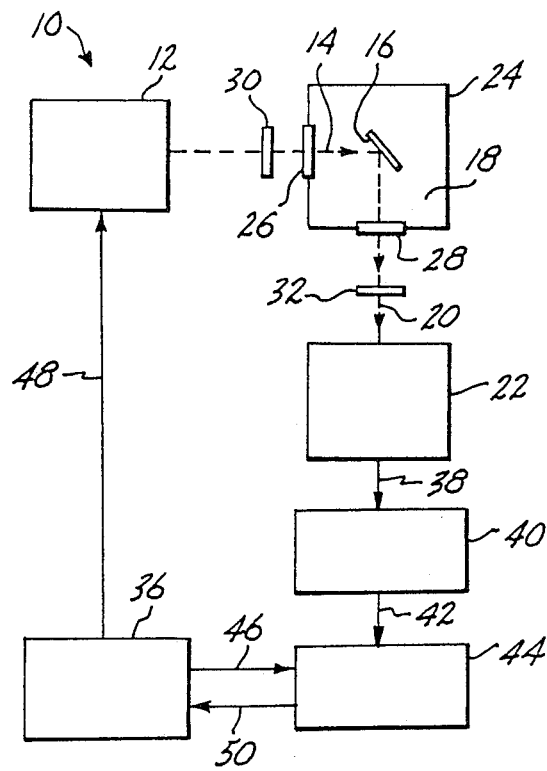
FIG. 1 is a block diagram of a representative system 10 for measuring oxygen concentration by the emission lifetime method of this invention.

The present invention addresses several previously unrecognized problems inherent in the prior art. In particular, we have found that the molecules studied by Eastwood and Gouterman are subject to photodecomposition when exposed to light and oxygen for extended periods of time. For best photostability the previously unreported fluorinated derivative platinum tetra(pentafluorophenyl)porphyrin, Pt(TFPP), must be used. (As used herein, the term "tetra(pentafluorophenyl)porphyrin" refers to the identical compound as the term "tetraperfluorophenylporphyrin" as stated in our referenced prior application.)

Furthermore, we have found that the phosphorescent emission decay in plastic is not a simple exponential, and so conventional methods of analysis fail to provide a measure of quenching that is useful over a wide range of oxygen pressures. In the next paragraphs we review the luminescence and quenching of aromatic molecules and then present our methods for using the observed nonexponential decay to accurately and conveniently determine oxygen concentration.

Photoexcitation of many molecular systems leads to metastable excited states that relax to the ground state by emitting light. Metastable photoexcited states are of two types: (i) those with the same spin as the ground state and (ii) those of different spin from the ground state. Emission from metastable excited states of type (i) is called fluorescence and is generally accomplished in under 0.2 microseconds. Emission from metastable excited states of type (ii) is called phosphorescence and is generally accomplished in times ranging from 1 microsecond to 20 seconds.

Both types of emission are quenched by oxygen. The first order decay rate of emission (k) of an excited state in the presence of oxygen is given by:

$$k = k_{nat} + k_d + k_q[O_2] = k_o + k_q[O_2] = 1/\tau \quad (1)$$

wherein $k_{nat}$ is the natural radiative lifetime of the metastable excited state, $k_d$ is the rate of any intrinsic radiationless decay processes, $k_q$ is the quenching rate of oxygen, $[O_2]$ is the oxygen concentration, and $k_o$ is the decay rate in the absence of oxygen. The inverse of k is called the emission lifetime, $\tau$.

The amount of light emitted by a sample is called the quantum yield, $\phi$, is defined as:

$$\phi = (\text{photons emitted/photon absorbed}) = k_{nat}/k. \quad (2)$$

It follows from Equations (1) and (2) that the quantum yield in the absence of oxygen, $\phi_o$, divided by the quantum yield in the presence of oxygen, $\phi$, given by:

$$\phi_o/\phi = 1 + k_q[O_2]. \quad (3)$$

Equations (1) and (3) are two forms of the Stern-Volmer equation for the effect of oxygen on quantum yield. This relationship is the basis for oxygen monitors that study the intensity of emission (I), which is directly proportional to quantum yield as follows:

$$I_o/I = 1 + k_q[O_2] \quad (4)$$

wherein $I_o$ and $I$ are respectively the emission intensities in the absence and presence of oxygen.

It can be seen that oxygen quenching can be determined by monitoring either decay rate as in Equation (1) or decay intensity as in Equation (4). For both types of measurements it is necessary to calibrate the sensor against reference solutions of known oxygen concentrations in order to determine the quenching parameter $k_q$. If decay rate is to be used, it is necessary to measure the emission intensity at a series of times, $t_1, t_2, t_3 \ldots$, after the exciting light has terminated. For a simple exponential decay two such timed measurements will suffice, and decay rate is determined from the equation:

$$k = (t_2 - t_1)^{-1} \ln[I(t_1)/I(t_2)]. \quad (5)$$

If intensity is used as in Equation (4), then it is necessary to reference intensity $I$ to the intensity $I_o$ in the absence of oxygen. As mentioned above, Stevens proposed obtaining $I_o$ from a second probe from which oxygen is excluded by an oxygen impermeable varnish.

The Stevens configuration is impractical for fiber optic probes. Lubbers and Peterson determine $I_o$ from scattered light. Both methods of measuring $I_o$ have the intrinsic limitation that they do not take account of photodegradation of the sensing molecule that may occur during the operation and that would reduce light output. Also, depending on the ability to manufacture exactly identical sensors, each particular probe may need calibration. Accordingly, Peterson calibrates each probe at three points: no oxygen, oxygen at the pressure of air, and at an intermediate oxygen pressure.

In contrast to the intensity measurement of Equation (4), the decay rate measurement of Equation (5) avoids difficulties caused by variability in sensor manufacture and by photodegradation. However, the oxygen sensors of Stevens, Lubbers et al., and Peterson et al. are all based on the quenching of fluorescence, which decays generally in under 0.1 microsecond ($\mu$s) and so requires fast electronics and fast light flashes to measure decay rate. This may account for their preferred use of the intensity ratio of Equation (4). The molecule used in the preferred embodiment of our oxygen sensor has a decay time in the 100 $\mu$s time range, so that slower electronics and exciting light flashes can be used, making the study of quenching through decay rate very practical. Furthermore, the use of decay rate as in Equation (1) rather than intensity ratio as in Equation (4) in principle makes our sensor insensitive to both variation in the probe manufacture (e.g., small variations in plastic thickness and emitter concentration) and to the formation of nonluminescent photoproducts during operation. In principle no calibration is necessary, but in practice we have found that one point calibration in air increases the accuracy of measurement by different probes.

While Equations (1) and (4) are generally considered to be equivalent measures of oxygen quenching, a serious problem arises in determining decay rate of aromatic molecules in plastic, since we find that such decay is generally nonexponential. That is, the decay time of luminescent aromatic molecules in plastic cannot be fit by a simple exponential but must rather be considered as a sum of two exponentials:

$$I(t) = A_1 e^{-k_1 t} + A_2 e^{-k_2 t} \tag{6}$$

wherein e is the exponential function. The four fitting parameters $A_1$, $k_1$, $A_2$, $k_2$ can be fit if I(t) is measured at many times t following an interval of photoexcitation. This type of determination requires considerable instrumentation and software analysis that may not be practical for routine operation. Furthermore, even given the knowledge of these four parameters, it is not clear how best to employ them to determine oxygen concentration because in the absence of an exponential decay the Stern-Volmer Equations (1) and (3) no longer apply.

To overcome these problems, we provide molecules having a decay time sufficiently long so that oxygen concentration can be conveniently determined through a measurement of the time dependence of emission intensity, i.e., I(t). We thereby avoid problems due to variations in probe construction and photodegradation that arise using methods that measure total intensity and its ratio to a reference, i.e., as in Equation (4). We also provide convenient methods of determining oxygen concentration from the function I(t), even though I(t) is non-exponential.

FIG. 1 shows a representative system 10 for determining the oxygen concentration of gaseous samples by measuring the quenching of various emitting sensor compositions in plastic. A flashing light source 12 (e.g., Strobotac Model No. 1538A) provides time dependent light excitation (indicated by dashed arrow 14) of an oxygen quenching-sensitive composition, which is sequestered in film 16 in this embodiment. Film 16 is mounted inside the fluid, depicted as vapor 18 here, that is to be sampled. Phosphorescent light (dashed arrow 20) emitted from film 16 impinges on a photodetector 22 (e.g., RCA 7265). A housing 24 containing windows 26, 28 can be used to isolate film 16 inside the fluid 18 being monitored, which is typically not identical with the environment of the rest of system 10. Windows 26, 28 can be made of quartz or glass.

Key components of system 10 are filters 30, 32. Filter 30 is a band-pass filter (e.g., Ealing 35-3649) that allows only shorter wavelength light 14, e.g., wavelengths in the range 480 to 600 nanometers (nm), to impinge on film 16. The range of band-pass filter 30 is chosen to match the region of strong absorption by the phosphorescing compound that is sequestered in film 16. Filter 32 is a cutoff filter (e.g., Corning 261) that allows only long wavelength light 20, e.g., wavelengths longer than 620 nm, to impinge on photodetector 22 and is chosen to allow the phosphorescent light 20 to reach the photodetector 22. In a preferred embodiment, the band-pass of filter 30 and the cutoff of filter 32 are complementary such that no light 14 from flashing light source 12 reaches photodetector 22.

The electric output (arrow 38) of photodetector 22 passes into preamplifier 40 of standard design. In the embodiment shown here, the output (arrow 42) of preamplifier 40 passes into a transient recorder 44 (e.g., Biomation Model No. 805) that is capable of sampling intensity, $I(t_1)$, at time intervals below a microsecond. The timing of system 10 is under control of microcomputer 36. In a preferred mode of operation that provides a zero baseline, microcomputer 36 puts out a trigger (arrow 46) to active transient recorder 44 and after a slight delay on the order of 20 microseconds puts out another trigger (arrow 48) to start flash light source 12. Transient recorder 44 thus collects data relating to $I(t_1)$, the intensity I of phosphorescence at various times $t_1$ before and after the flash, which data are read (as indicated by arrow 50) into the computer 36.

Flash rates using system 10 are typically on the order of 100 per second. The time interval between successive flashes 14 is sufficiently long that a decay time and hence oxygen concentration can be calculated after each flash 14. It should be noted that the limiting time of response is set by the diffusion rate of oxygen into the monitor film 16, which is typically under one second. This diffusion rate becomes faster, permitting response times on the order of milliseconds, with thinner films 16 and by adding plasticizer to the carrier matrix, as described below. Thus, real-time measurements of oxygen concentrations can be made by this method.

Figure 2:
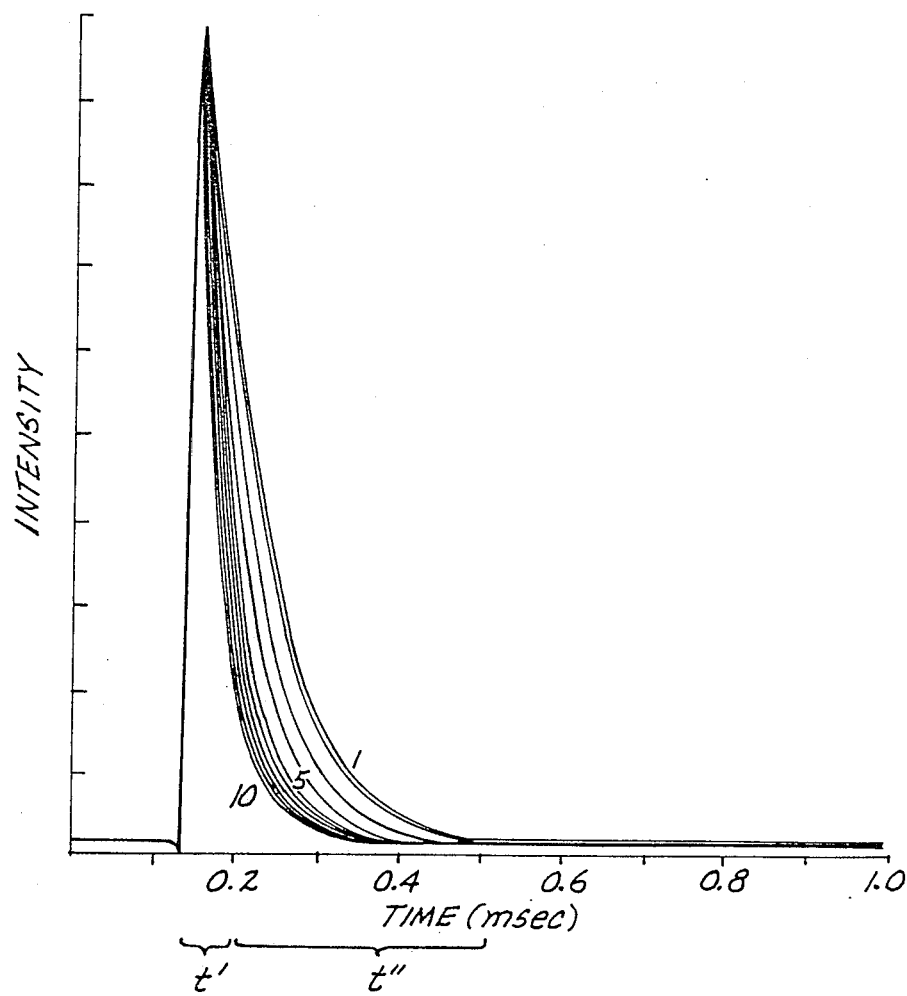
FIG. 2 is a graph showing phosphorescence emission of Pt(TFPP) decay curves as a function of molecular oxygen pressures, as described in Example 1.

Pursuant to this disclosure, measurement is made of the intensity, $I(t_i)$, of phosphorescence 20 emitted by the film 16 at a series of times, $t_1, t_2, t_3 \ldots$, after the flash 14. The light intensities $I(t_i)$ at any particular time $t_i$ following several flashes can e averaged. A decay rate, k, of the phosphorescence is calculated from these data by the computer 36 using various algorithms. In particular, with a full set of values $I(t_i)$ we can fit the decay to Eq. (6) above. Decay curves for Pt(TFPP) in polyvinyl chloride with plasticizer are shown in FIG. 2, wherein t' is the period of linear decay, i.e., where $\Delta I/\Delta t$ has a constant slope at any particular oxygen pressure of interest, and wherein t" is the remaining period of the detectable emission, during which $\Delta I/\Delta t$ is not constant. Representative values found for the fitting parameters $A_1, k_1, A_2, k_2$ are listed in Table 1.

TABLE 1

Data analysis of PtTFPP in PLS/PVC[a,b,c].

| pO2 | A1 | k1 | A2 | k2 | $\bar{k}$ | $\bar{\tau}$ | $\bar{k}/k_o$ | $\tau_o/\bar{\tau}$ |
|---|---|---|---|---|---|---|---|---|
| 1 | 1. | 13.1 | | | 13.1 | 73.3 | 1. | 1. |
| 10 | 0.88 | 13.26 | 0.12 | 24.2 | 14.6 | 71.3 | 1.11 | 1.07 |
| 50 | 0.78 | 15.03 | 0.22 | 26.5 | 17.6 | 60.3 | 1.34 | 1.27 |
| 100 | 0.64 | 16.23 | 0.36 | 31.4 | 21.7 | 50.9 | 1.66 | 1.50 |
| 200 | 0.63 | 18.25 | 0.31 | 41.5 | 26.8 | 43.4 | 2.05 | 1.76 |
| 300 | 0.58 | 19.23 | 0.42 | 45.4 | 30.2 | 39.4 | 2.30 | 1.94 |
| 400 | 0.33 | 17.0 | 0.67 | 39.4 | 32.0 | 36.5 | 2.44 | 2.09 |
| 500 | 0.305 | 17.2 | 0.695 | 41.1 | 33.8 | 34.6 | 2.58 | 2.20 |

[a]PLS/PVC = plasticized polyvinyl chloride; see Example 1 for details.
[b]Data taken by system 10.
[c]The k's are in $(ms)^{-1}$, and $\bar{\tau}$ is in $\mu s$.

Two measures for the time decay can be defined: Average decay rate, $\bar{k}$, is given by:

$$\bar{k} = (A_1 k_1 + A_2 k_2)/(A_1 + A_2). \quad (7)$$

Average decay time, $\bar{\tau}$, corresponds to the normalized integral of the emission intensity, $I(t)$, as follows:

$$\bar{\tau} = (A_1 k_1^{-1} + A_2 k_2^{-1})/(A_1 + A_2). \quad (8)$$

Figure 3:
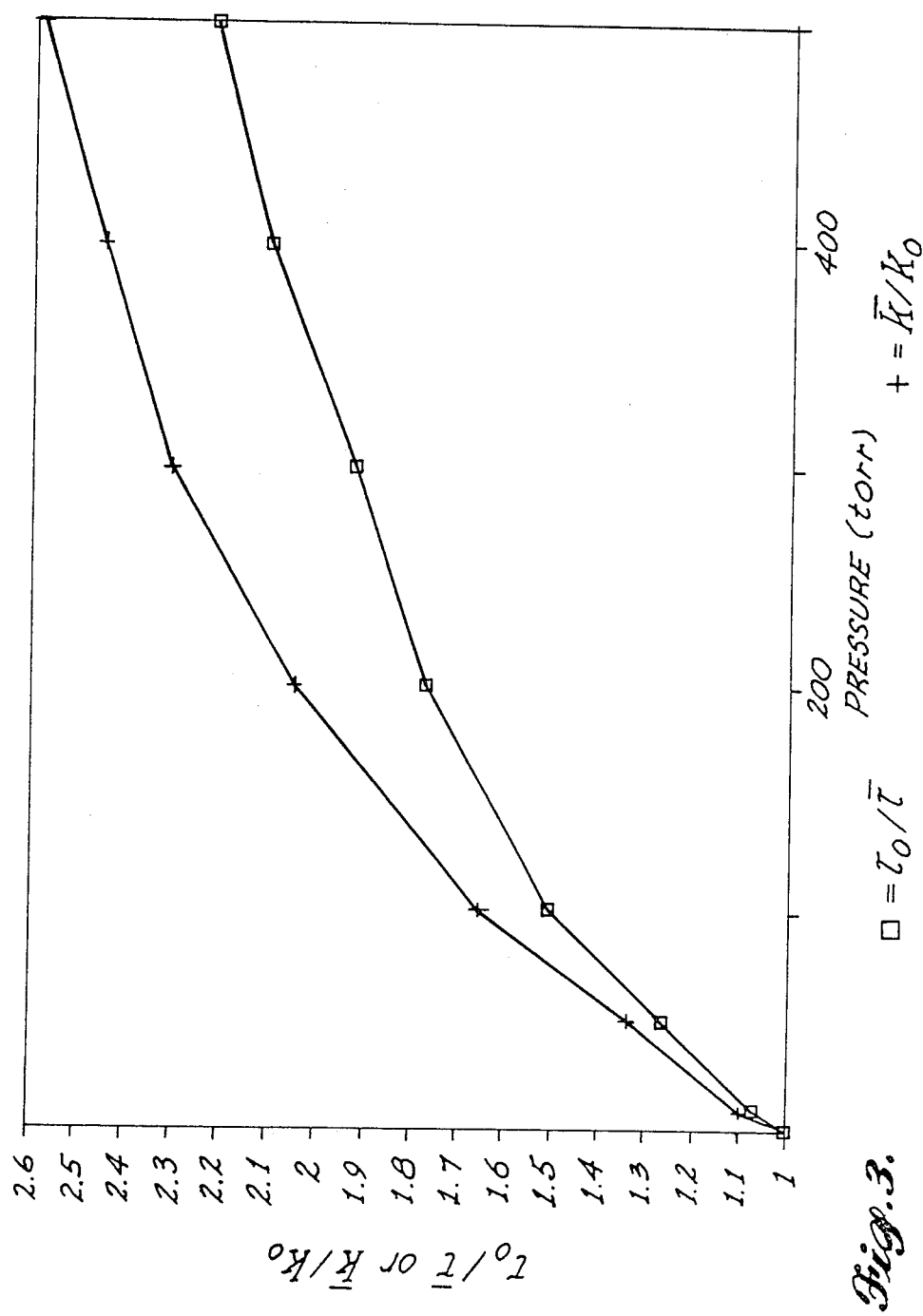
FIG. 3 is a graph plotting $\bar{k}/k_o$ and $\tau_o/\tau$ versus $pO_2$ for the decay curves shown in FIG. 2 and the data presented in Table 1.

$\bar{\tau}$ represents the total amount of light emitted following termination of excitation, which has been the principal measure of oxygen quenching in the prior art; however, the prior art did not consider the disclosed nonexponential decay phenomenon. The value $\bar{k}$ corresponds to the normalized decay rate at t=0. in FIG. 3 we plot representative $\tau_o/\bar{\tau}$ and $\bar{k}/k_o$ curves using the data listed in Table 1. These curves would be identical for an exponential decay. FIG. 3 shows that $\bar{k}/k_o$ gives a more linear Stern-Volmer plot; hence $\bar{k}$ provides a more accurate determination of oxygen concentration at higher oxygen pressures.

The double exponential decay of Eq. (6) can be understood as resulting from two types of emitting molecules: Those with larger $k_1$ are more subject and those with smaller $k_2$ are less subject to quenching by oxygen. The average decay time, $\bar{\tau}$, gives heavier weight to the unquenched molecules, whereas the average decay rate, $\bar{k}$, gives heavier weight to the quenched population and provides a better measure of oxygen quenching.

In a related method, the slope of the emission profile during the period of linear decay is compared with similarly obtained slopes for fluids of known oxygen concentrations. Due to the double exponential nature of the luminescent decay curve, the referenced slope values must not encompass any of the tail region (t" in FIG. 2) of the emission profile. Once this relationship is established, the time it takes for the intensity of emission to fall to any particular level within time t' can provide a convenient readout of pO2. Alternatively, the intensity measured with the test fluid at any particular time t less than t' can be compared with standard curves of intensity versus time (again, less than t') for a series of fluids of known oxygen concentrations.

Figure 4:
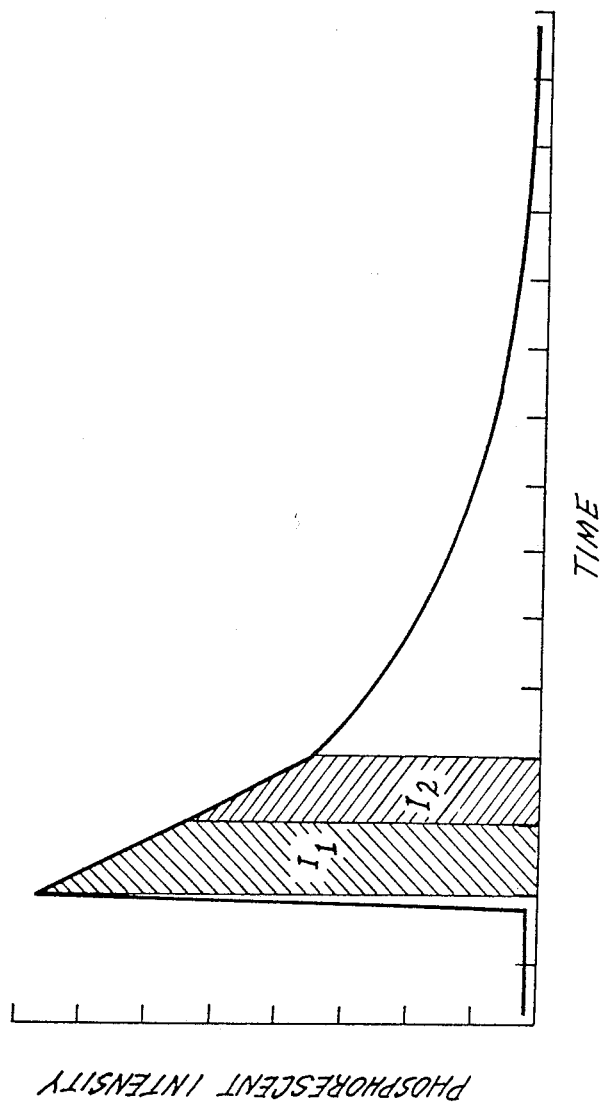
FIG. 4 is a representative plot showing the two intensity segments $I_1$ and $I_2$ as used in Equation (9) in conjunction with system 10.
Figure 5:
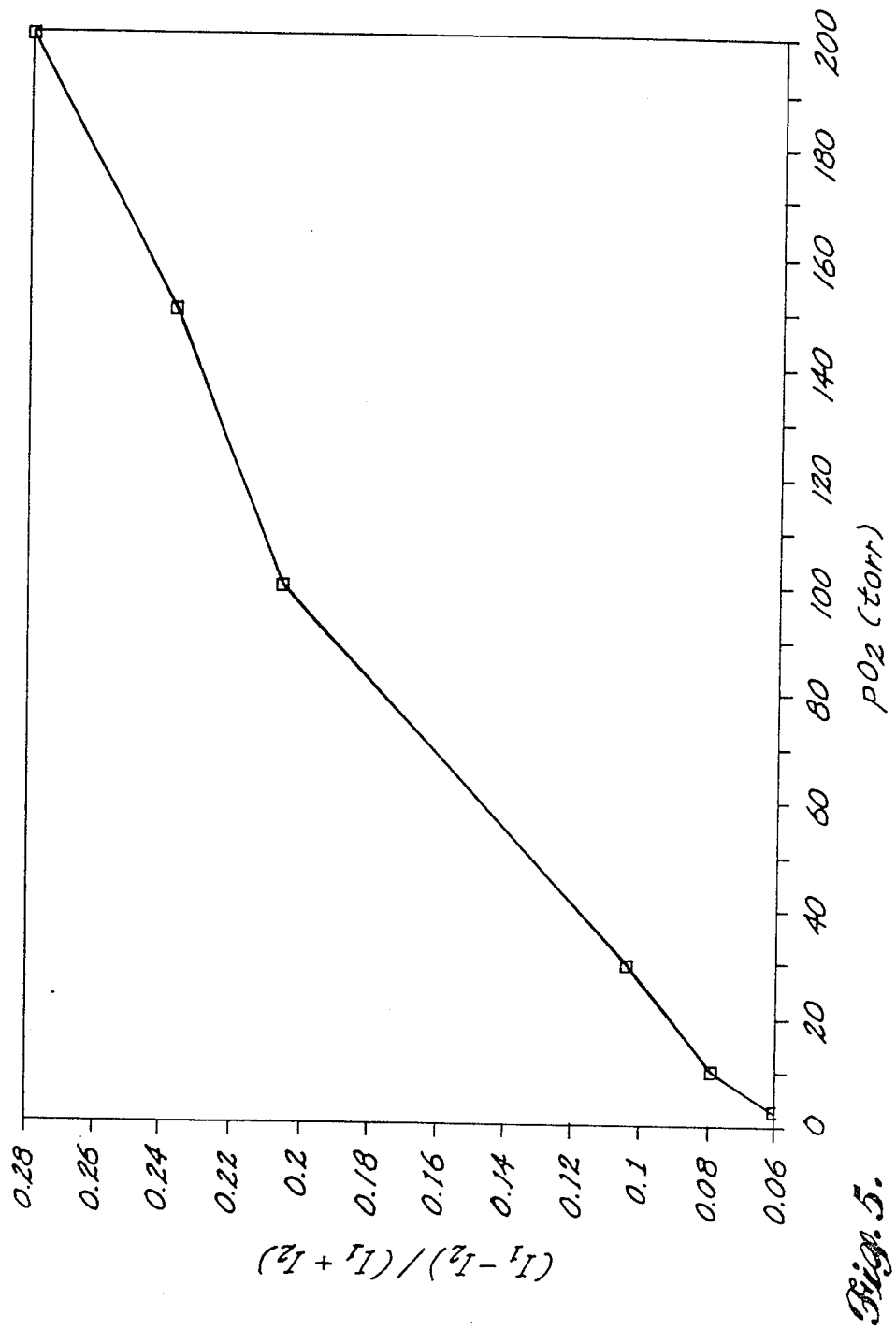
FIG. 5 is a plot of R versus $pO_2$ for the embodiment shown in FIG. 4.

We have also discovered other convenient methods of measuring pO2, taking into consideration the nonexponential decay of luminescent molecules in plastic. The following methods reference one time segment of emission against another and thus provide measurements that are independent of sensor configuration or light path variation. With system 10, the best measure for oxygen quenching is the intensity ratio, R, given by:

$$R = (I_1 - I_2)/(I_1 + I_2), \quad (9)$$

wherein $I_1$ and $I_2$ are the sums of the intensities, or total flux of luminescent light, measured by the transient recorder during two time periods that together substantially encompass the period of linear decay of the luminescent emission once the light source 12 is turned off. With systems 10, the time intervals for $I_1$ and $I_2$ can be readily optimized for particular combinations of luminescent substance, matrix, and oxygen pressure range of interest by sampling time intervals and selecting those that provide the best resolution within the linear decay period. For example, with a Pt(TFPP) film 16, $I_1$ can be the flux of phosphorescence detected over times from 0 to 10 $\mu s$, and $I_2$ can be the sum of the intensities over times from 10 to 20 $\mu s$, with time zero for both measurements being the end of the period of illumination. FIG. 4 illustrates the two intensity segments $I_1$ and $I_2$, and a corresponding plot of R versus pO2 (oxygen pressure) is shown in FIG. 5. It is not necessary for the selected time intervals to encompass the entire period of linear decay. However, $I_1$ and $I_2$ preferably subdivide the period of linear decay (t' in FIG. 2) into two equal time periods.

The subject method can be used to measure oxygen concentration in a fluid, meaning gas and/or liquid. For example, the oxygen concentration in closed and semi-closed atmospheres 18 such as aircraft and mines can be measured using a detection system similar to 10, shown in FIG. 1. Oxygen concentrations in liquids such as blood, seawater, and sewage can also be monitored by the method of this invention.

Figure 6:
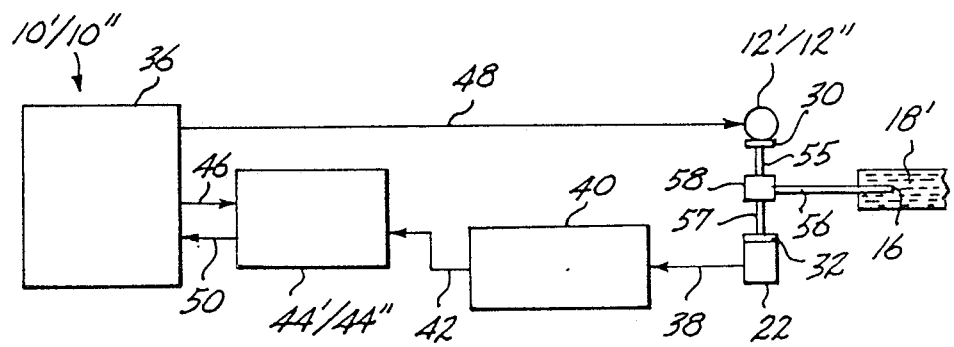
FIG. 6 is a block diagram of representative systems 10' and 10" suitable for monitoring oxygen concentration in the bloodstream.

FIG. 6 shows representative systems 10', 10" for monitoring oxygen in the bloodstream 18'. The following components are identical to those described above for system 10: electric output (arrow 38), trigger (arrow 46), trigger (arrow 48), data (arrow 50), sensing composition 16, phototube 22, filters 30,32, microcomputer 36, and preamplifier 40. In systems 10' and 10" the film 16 containing the oxygen quenching-sensitive composition is positioned at the end of an optical pipe 56, which carries the exciting light to and the emitted light from the film 16. In system 10' the exciting light source 12' is a flash lamp, while in system 10" the exciting light source 12" is a light emitting diode (LED). The exciting light from light source 12' or 12" passes into light pipe 55. The emitted light exits through light pipe 57. The light pipes 55, 56, 57 are connected by a standard three-way optical coupler 58 (e.g., GTE ATA No. OCL-0102-X). In system 10' the output 42 from the preamplifier 40 passes into a fast A/D converter 44' (e.g., the LAB-40 manufactured by Computer Continuum, Daly City, CA 94015). In system 10" the output from the preamplifier 40 passes into a specically designed electronic circuit 44", termed herein an integral ratio determinator, which calculates R" using Eq. (11) below.

Figure 8:
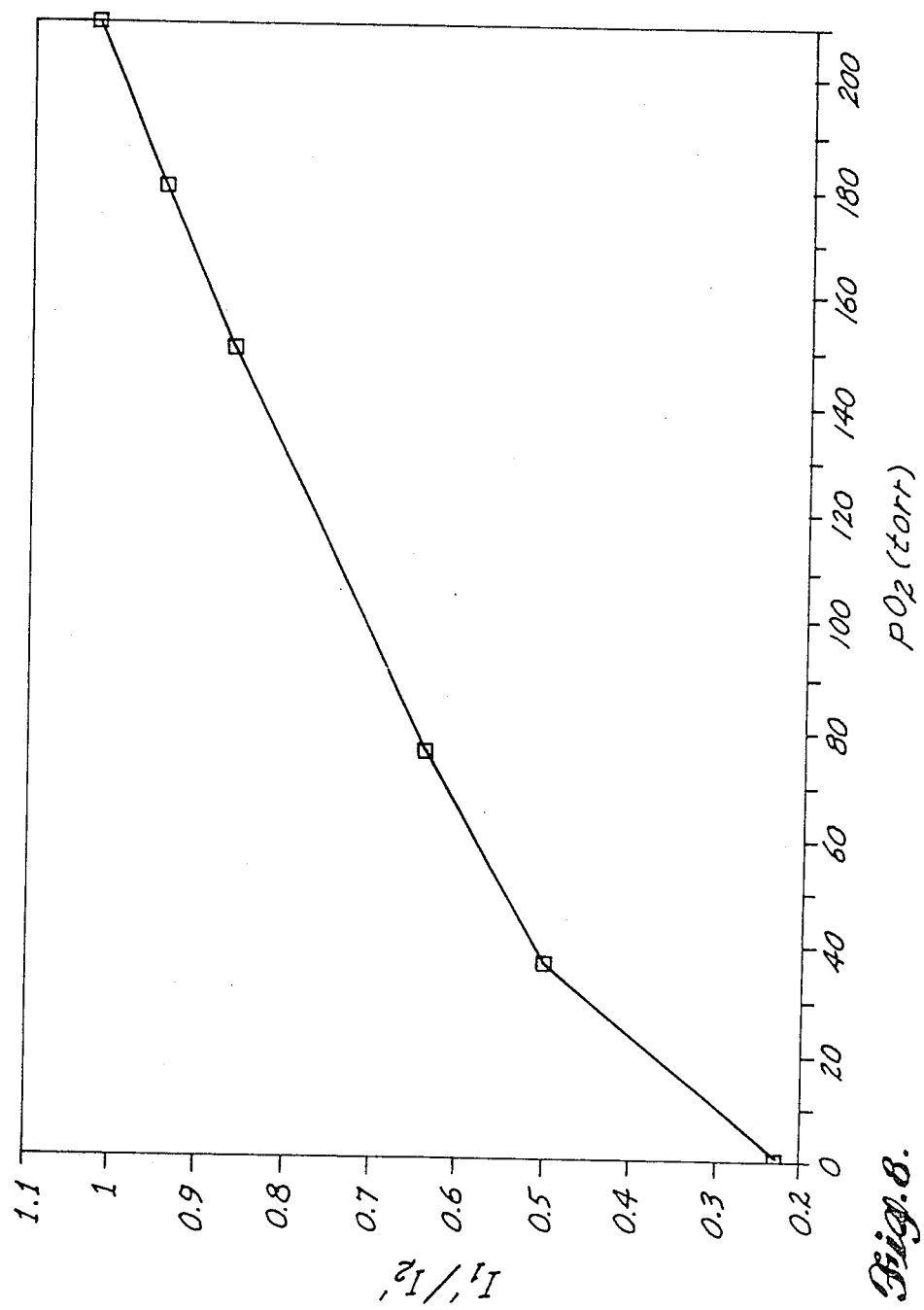
FIG. 8 is a plot of R' versus $pO_2$ for the embodiment shown in FIG. 7.

Using system 10', oxygen quenching is measured as the intensity ratio, R', given by:

$$R' = I_1'/I_2', \quad (10)$$

wherein $I_1'$ and $I_2'$ represent the fluxes of luminescence over two time periods that substantially encompass the period of detectable luminescent emission once the light source 12' is turned off. With system 10', time intervals are selected from the lamp-off regions of linear t' and nonlinear t" decay to provide ratioing R values of $I_1'$ and $I_2'$ that give the best resolution within the oxygen pressure range of interest. $I_1'$ preferably encompasses the period of linear decay of the luminescent emission. For example, with a Pt(TFPP) film 16, $I_1'$ can be the sum of the intensities $I(t_i)$ digitized by the fast A/D converter over times from 0 to about 20 μs, and $I_2'$ can be the sum of the intensities over times from 20 to 300 μs, with time zero for both measurements being the end of the period of illumination. FIG. 7 illustrates the two intensity segments $I_1'$ and $I_2'$, and a corresponding a plot of R' versus $pO_2$ is shown in FIG. 8.

Figure 9:
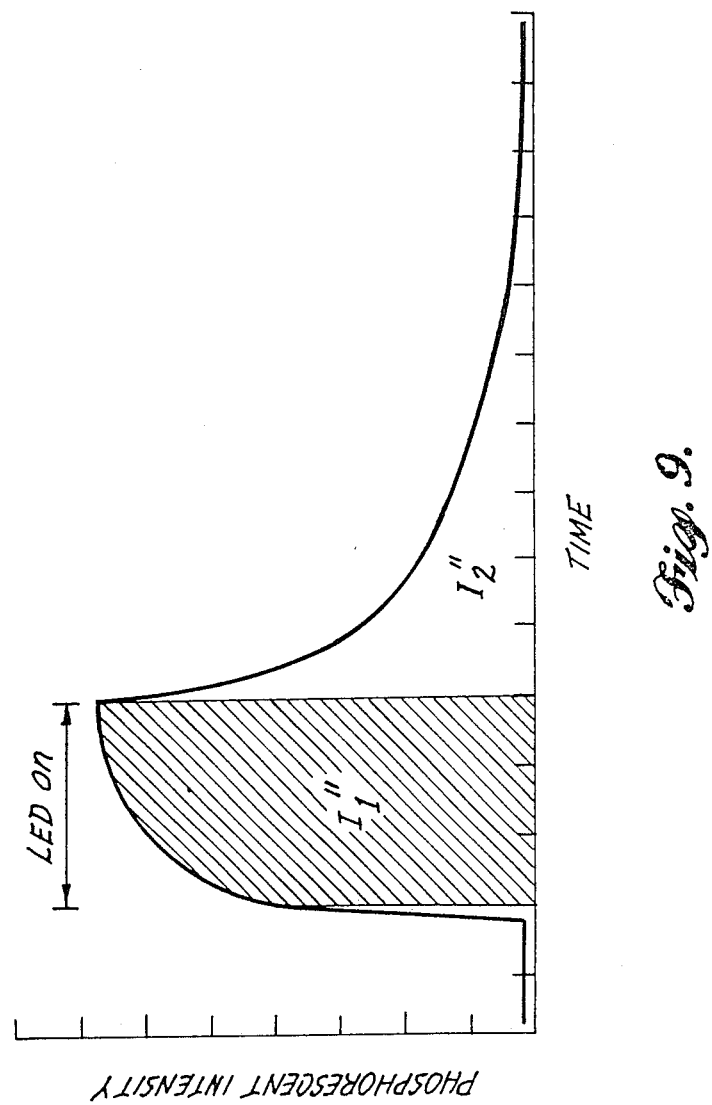
FIG. 9 is a representative plot showing the two intensity segments $I_1''$ and $I_2''$ as used in Equation (11) in conjunction with system 10"
Figure 10:
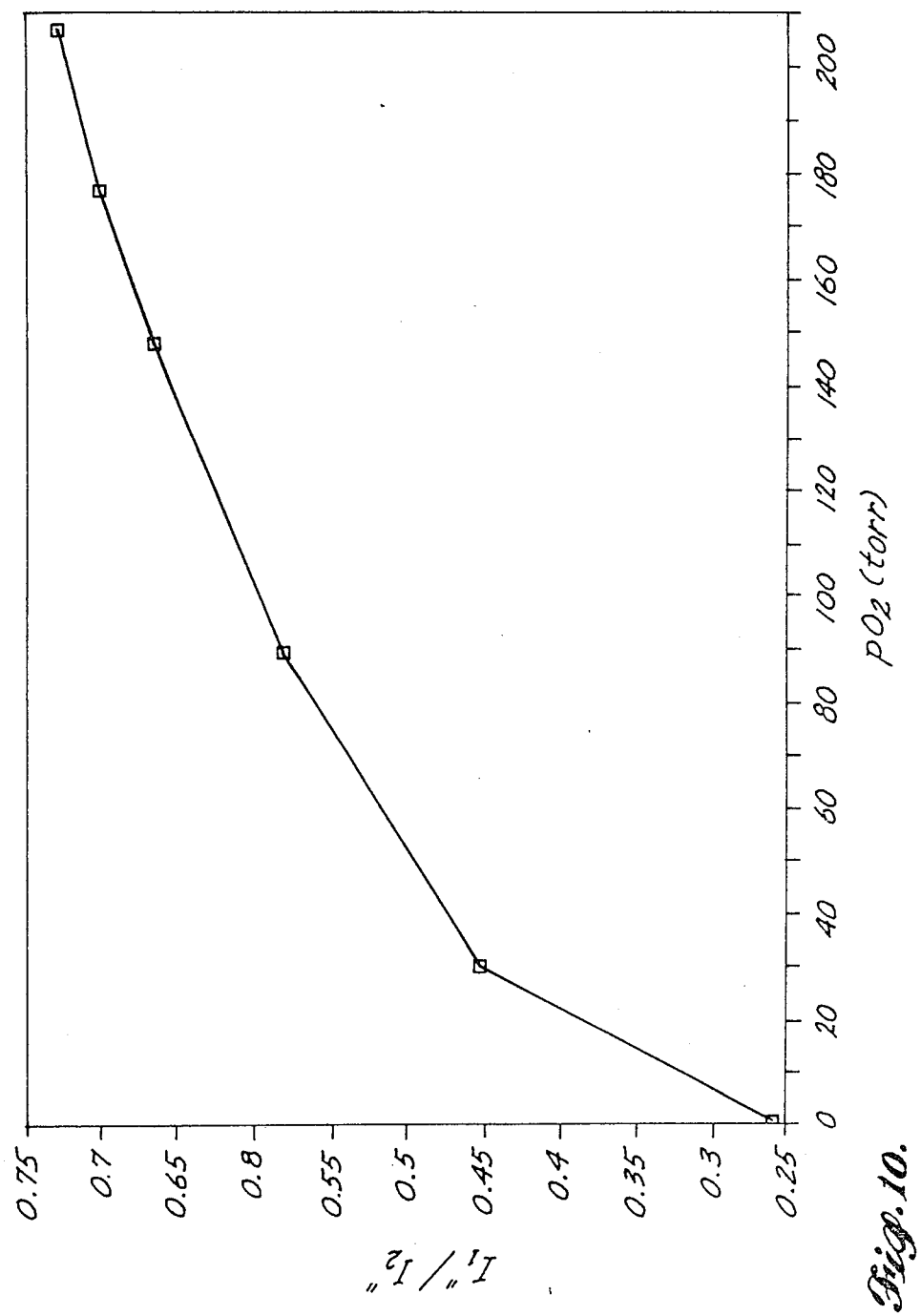
FIG. 10 is a plot of R" versus $pO_2$ for the embodiment shown in FIG. 9.

With system 10" the LED is turned on, for example, from time 0 to approximately 50 μs. Here the measure of oxygen quenching is the intensity ratio, R", given by:

$$R'' = I_1''/I_2'', \quad (11)$$

wherein $I_1''$ is the flux of luminescence during a first time interval taken before the light 12" is turned off, and $I_2''$ is the flux of emitted light during a second time interval taken subsequent to extinguishing the light source 12". $I_1''$ preferably encompasses the entire time period during which light source 12" is turned on, and $I_2''$ preferably encompasses substantially the entire period of detectable luminescent emission subsequent to turning off the light source 12". The light source 12" is most preferably turned on only until the detected luminescent intensity plateaus, meaning attains its maximum intensity, as shown in FIG. 9. For the representative Pt(TFPP) embodiment, $I_1''$ can be the intensity of emission gathered over the time period from 0 to 50 μs, i.e., while the LED is on, and $I_2''$ can be the intensity of emission gathered from 50 μs to 300 μs, after which there is no more emitted light. In the integral ratio determinator 44" the signal 42 from the preamp 40 is split by two balanced synchronous demodulators into the pulse and decay (light 12" on and off) components. Circuit 44" then integrates the pulse and decay components separately, passes the signals through V/F converter channels, and respectively counts each component for the digitized equivalent. FIG. 9 illustrates the two intensity segments $I_1''$ and $I_2''$, and a corresponding plot of R" versus $pO_2$ is shown in FIG. 10. We found with system 10" that apparently identical sensors give calibration plots of $pO_2$ versus R" that are parallel but shifted from one another. Thus, to obtain accurate values of $pO_2$ each sensor should be calibrated at one pressure, preferably the oxygen pressure of air.

The disclosed method uses as emitters metalloorganic molecules, in particular Pt and Pd derivatives of porphyrins. The organic region of these molecules is where light absorption and emission occurs, and this provides a strong absorption coefficient. Moreover, their natural phosphorescence decay rate, $k_{nat}$, has been greatly increased by the metal atom so they have a high quantum yield of phosphorescence. Furthermore, their phosphorescence decay time is sufficiently short so that it is in a convenient range to monitor for oxygen quenching.

A suitable oxygen quenching-sensitive monitor 16, or sensor composition, for practicing this invention contains at least one species of phosphorescent molecule having the following properties (a) through (i):

(a) The phosphorescent molecule should have a high absorption coefficient for light obtained from a convenient flashing light source.

(b) The quantum yield of phosphorescence should be large so that there is sufficient light to work with, roughly $\phi > 0.2$.

(c) The phosphorescence lifetime in the absence of oxygen should be in the range 50 microseconds to 5 milliseconds. With too short a lifetime, apparatus becomes more expensive. With too long a lifetime, the emission will tend to be entirely quenched in higher oxygen ranges of interest.

(d) The wavelengths of strong absorption and strong emission should be well separated so that complementary filters can be obtained to isolate these spectral regions.

(e) The emission should be in the red, with wavelengths longer than 600 nanometers, as this avoids competition from extraneous emission that might occur from the sample or from windows, filters, and optical pipes.

(f) The phosphorescent molecule should be stable to photooxidation, since they will be used under illumination and with oxygen present.

(g) The phosphorescent molecule should be insoluble in the fluid being monitored so that it does not leach out of the monitor. For example, for monitoring blood the molecule should not be water soluble. On the other hand, the molecule must have solubility suitable for monitor fabrication.

(h) The natural and radiationless decay times, $k_{nat}$ and $k_d$ in Eq. (1), should be insensitive to small temperature changes.

(i) The emission properties should not be sensitive to common molecules, e.g., $H_2O$, $CO_2$, $N_2$, and to other molecules likely to be present in the fluid to be monitored, e.g., halothane or N₂O in blood.

The phosphorescent molecule(s) having the foregoing properties can be sequestered in a carrier matrix to form an oxygen monitor 16. The following characteristics (j) through (l) apply to both the phosphorescent molecule and the carrier matrix:

(j) The phosphorescent molecule(s) and the carrier matrix should be chemically stable, so that they do not deteriorate.

(k) The phosphorescent molecule(s) and the carrier matrix should not be toxic.

(l) The phosphorescent molecule(s) and the carrier matrix should be conveniently synthesized or purchased.

The following properties (m) through (s) apply to the carrier matrix, which is preferably an oxygen-permeable plastic:

(m) The carrier matrix should dissolve or bond with the phosphorescent molecule and be easily cast onto the substrate which holds it.

(n) The carrier matrix must be porous to oxygen and should equilibrate over convenient times, since this equilibration rate determines the response time of the oxygen monitor. We have found that the response time can be shortened by the amount of plasticizer in a PVC carrier matrix.

(o) For oxygen concentrations, $[O_2]_{fl}$, of interest in the fluid being monitored, the equilibrium oxygen concentration in the carrier matrix, $[O_2]_{mx}$, and the quenching constant, $k_q$, should be of size:

$$k_q[O_2]_{mx} \, k_{nat} + k_d \qquad (9)$$

wherein these quantities are those of Eq. (1). If the left side of Eq. (9) is much larger than the right side, then little emission is observed; if the left side is much smaller than the right side, then little quenching is observed. Thus the product $k_q[O_2]_{mx}$ must be adjusted to match the parameters $k_{nat}+k_d$ of the phosphorescing molecule and the oxygen concentration $[O_2]_{fl}$ in the fluid to be monitored.

(p) The carrier matrix should stick to the substrate on which it is mounted, e.g., the end of a light pipe 56 as in FIG. 6.

(q) The carrier matrix should be nonvolatile and insoluble in the fluid being monitored.

(r) The carrier matrix should be chemically stable with respect to the fluid being monitored, the phosphorescent molecule in its ground state, and the phosphorescent molecule in light in the presence of oxygen.

(s) Finally, the carrier matrix should be transparent to the exciting light and to the phosphorescent light.

Suitable oxygen quenching-sensitive phosphorescent molecules for practicing this invention include prophyrins, meaning those compounds that contain the porphyrin ring structure (Monograph No. 7468, Tenth Edition of The Merck Index, Merck & Company, Inc., Rahway, NJ, 1983), chlorins, bacteriochlorins, and isobacteriochlorins. The porphyrin ring structure gives rise to intense optical absorption and emission in the wavelength range of interest. The wavelengths for absorption and emission can be shifted by various chemical modifications to the porphyrin ring structure. In addition, the emission lifetimes and quantum yields are strongly dependent on any metal incorporated into the center of the ring. The preferred synthetic rings for employment in the practice of this invention are tetra(pentafluorophenyl)porphyrin (TFPP), octaethylporphyrin (OEP), tetraphenylporphyrin (TPP), and tetrabenzporphyrin (TBP) compounds. Preferred metals are second and third transition row metals with electron configurations $d^6$ or $d^8$, including Ru(II), Rh(III), Pd(II), Os(II), Ir(III), Pt(II), and Au(III). All of the aforementioned metalloporphyrins show phosphorescence with moderate quantum yields and suitable lifetimes. However, the Pd(II) and Pt(II) derivatives are the most preferred since only they are free of axial ligands and/or counter ions, which can complicate the synthesis and can introduce instabilities either during film preparation or during operation under light; moreover, they have the highest quantum yields of emission. Some other metalloporphyrins may also be suitable; for example, we have had some success using Hf(IV) octaethylporphyrin.

Pd(II) and Pt(II) complexes of tetra(pentafluorophenyl)porphyrin (TFPP), octaethylporphyrin (OEP), tetraphenylporphyrin (TPP), and tetrabenzporphyrin (TBP) have proven in our hands to be the best phosphorescent molecules for practicing this invention as they tend to satisfy most of the above-stated criteria (a) to (i). Moreover, the palladium, Pd(II), porphyrins have lifetimes in the absence of oxygen of 1-2 milliseconds and the platinum, Pt(II), porphyrins of around 100 microseconds. As a result, these Pd(II) and Pt(II) porphyrins are most sensitive in different regions of oxygen concentration: In particular, the palladium porphyrins are best used under 10 torr pressure, while the platinum prophyrins can best be used above 50 torr pressure. By employing in the oxygen quenching-sensitive composition a combination of different phosphorescent molecules having different phosphorescent lifetimes, e.g., any of the above-stated Pd porphyrins along with any of the above-stated Pt porphyrins, a wider range of oxygen pressures can be monitored than by use of either phosphorescent molecule alone.

We have also discovered that the range of sensitivity for any particular phosphorescent molecule used in the oxygen quenching-sensitive composition can be adjusted by choice of the carrier matrix and also the amount of plasticizer dissolved in the matrix. Polyvinyl chloride with variable amounts of plasticizer provide suitable carrier matrices, as does polymethyl methacrylate without plasticizer. Other suitable oxygen-permeable matrices can be made of cellulose acetate or silicone-polybicarbonate copolymer (Petrarch MB).

We have also discovered that Pd and Pt tetraphenylporphyrin and tetra(pentafluorophenyl)porphyrin show a specific absorption band proportional to the deterioration of the compound. This band lies in the wavelength range 550–620 nm, depending on the compound. This new band may be due to a photooxidation product. The appearance of the specific band upon prolonged irradiation can be used to provide a quality control check of photodeterioration to determine when the monitor film should be changed.

As mentioned above, the Pd(II) and Pt(II) porphyrins with the rings OEP, TBP, TFPP, and TPP are the preferred phosphorescent molecules for use in the disclosed measurement methods. All of these preferred molecules are in addition reasonably stable when freshly synthesized and over the time course of typical laboratory analyses of absorption and emission properties. However, we found that some of these eight species proved less stable than others when subjected to extended illumination and ambient oxygen. Not all of the Pd and Pt porphyrins in polyvinyl chloride containing plasticizer are sufficiently stable under extended illumination to be suitable for oxygen sensors. The OEP and TBP rings deteriorated so readily that they were entirely gone, as evidenced by lack of absorption spectrum, after fifteen hours of illumination. The TPP ring proved more hardy and showed a survival of emission intensity and lifetime slightly poorer than perylene dibutyrate (PDB), the molecule of choice for a fluorescent oxygen sensor described in U.S. Pat. No. 4,476,870 and in Anal.Chem. 55:62–67, 1984. The TFPP ring proved more hardy than PDB under the same test conditions. The survival of the emission intensity of Pd(TFPP) was comparable to that of PDB, while that of Pt(TFPP) was better. The emission intensity of the Pt(TFPP) after 15 hours of illumination was 80% of its initial value while the lifetime was 95% of its initial value.

Since luminescent compounds are quite generally photooxidized in the presence of oxygen, it is critical to select a relatively photostable phosphorescent or fluorescent molecule for use in luminescent oxygen sensors. The most preferred phosphorescent molecules for monitoring oxygen concentration by any of the previously reported or subject methods therefore include Pd(TFPP) and Pt(TFPP).

Photooxidation of aromatic molecules is one of the most important processes by which compounds are degraded and undergo permanent chemical transformations. In general, photooxidation reactions of aromatic compounds are enhanced by more extended conjugation, higher electron density, and lower oxidation potentials. Porphyrin reactivity with molecular oxygen in the presence of light is influenced by the inductive effects of the functional group attached either at the periphery of the porphyrin ring or in extraplanar ligands. In the case of TFPP systems we observed that the electron withdrawing effect of the pentafluorophenyl substituents raises the oxidation potential and reduces the electron density. These factors make the TFPP molecules less reactive toward photooxidation process and increase its photostability. The measured oxidation potentials of a series of free base porphyrins are shown in Table 2.

| Compound | Porphyrin oxidation potential. $E_{\frac{1}{2}}^{ox}$ [Volts] | Reference |
|---|---|---|
| H$_2$OEP | 0.81 | J. Amer. Chem. Soc. 85:140, 1973. |

-continued

| Compound | Porphyrin oxidation potential. $E_{\frac{1}{2}}^{ox}$ [Volts] | Reference |
|---|---|---|
| H$_2$ETIO | 0.77 | J. Phys. Chem. 229:259, 1964. |
| H$_2$TPP | 0.97 | J. Phys. Chem. 229:259, 1964. |
| H$_2$TFPP | 1.6 | Our unpublished data. |

Recently we have optically studied the pi-cation formed when thin film samples of various porphyrins, including Zn(TFPP), are exposed to various partial pressures of molecular oxygen and light. This work clearly showed that the concentration of cation formed depends upon the porphyrin ring oxidation potential. The Zn(TFPP) showed no evidence of cation formation when exposed to 760 torr oxygen and white light for 24 hours.

Pursuant to this aspect of the invention, other aromatic molecules can be made more photostable by substituting fluorine atoms on the periphery of the synthetic ring. Such complete or partial fluorine substitutions make the luminescent molecule less susceptible to photodeterioration. Photodeterioration is indicated by a diminution following exposure to illumination of the molecule's absorption spectrum and/or its emission peak ratios and lifetime ratios. The first step in photodeterioration probably involves electron loss from the luminescent molecule to ambient oxygen molecules, and we believe that the fluorinated sidegroups inhibit such transfers. We have also observed that such fluorination serves to protect the integrity of the phosphorescent molecule's emission lifetime profile more than its emission intensity. Thus, these fluorinated porphyrins are particularly well-suited for monitoring oxygen concentration using the disclosed emission lifetime method.

Closely related molecules to Pd(TFPP) and Pt(TFPP) that may retain the advantage of photostability are the reduced ring chlorin (dihydroporphyrin), bacteriochlorin (opposite tetrahydroporphyrin), and isobacteriochlorin (adjacent tetrahydroporphyrin); described in M. Gouterman, Chapter 1, pp. 1–165, in The Porphyrins, Vol. III, D. Dolphin, Ed., Academic Press, N.Y. 1978, expressly incorporated herein by reference. We have effected ring reduction of Pt(TFPP) using a two-fold excess of paratoluenesulfonylhydrazine, K$_2$CO$_3$ (anhydrous in pyridine) at 100° C. for a few hours, using the method of Whitlock et al., J.Amer.-Chem.Soc. 91(26):7485–7489, 1969, expressly incorporated herein by reference. The reduced porphyrins of these and the other mentioned porphyrins have the advantage that their absorption is redshifted to a region for which light emitting diodes can be used for excitation.

Another preferred group of photostable, phosphorescent molecules for incorporation in oxygen quenching-sensitive compositions must include Pd(II) and Pt(II) derivatives of fluorine substituted tetrabenzporphyrin (TBP), shown below and abbreviated TFBP.

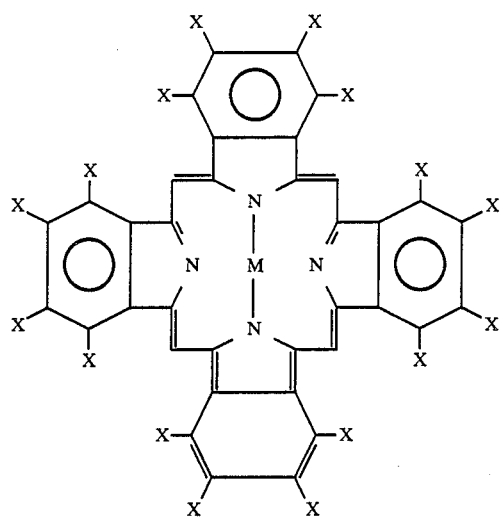

M = Pd, Pt
X = H:TBP    I
All of X = F:TFBP    II
Any of X = F    III

Because of the greater electron withdrawing power of fluorine with respect to hydrogen, TFBP molecules are expected to prove more stable than TBP to photooxidation when exposed to light and oxygen. Partial fluorination to give compounds of formula III should also enhance photostability.

Although the Pd and Pt tetrabenzporphyrins proved unstable under extended illumination, they exhibit certain other advantages as compared with the TFPP derivatives. In particular, since the TBP absorption maxima are further to the red, they are more suitable for excitation by available light emitting diodes. Also, since their emission is further to the red than Pt(TFPP) it is less absorbed by optical piping and is less subject to interference by extraneous emission. Thus it is contemplated that Pd(II) and Pt(II) derivatives of the above-stated molecules II or III will provide photostability as well as a more convenient spectral range.

The following illustrative but nonlimiting examples further illustrate the invention.

EXAMPLE 1

Pt(TFPP) in PVC

Free base tetra(pentafluorophenyl)porphyrin, H$_2$(TEPP), was made following Longo et al., *J.Heterocycl.Chem.* 6:927, 1969. H$_2$(TFPP) was purified by the procedure of Spellane et al., *Inorg.Chem.* 19:386, 1980, a paper that describes preparation of Pd(TFPP). Pt(TFPP) was made from H$_2$(TFPP) and a 10 times molar excess of PtCl$_2$ (Aldrich Chemical Co.) refluxed for 24 hours in benzonitrile. The product was chromatographed on neutral alumina column with CH$_2$Cl$_2$ as eluant. 10 mg of the Pt(TFPP) were then dissolved in a 25 ml aliquot of a PVC stock solution made by dissolving 3 grams of polyvinyl chloride (PVC; B.F. Goodrich) in 70 ml tetrahydrofuran and 200 ul of 2-nitrophenyl-octylether (Fluka AG) as plasticizer. Samples are prepared by casting the resulting solution on a glass slide and allowing the tetrahydrofuran to evaporate. Films prepared in this manner were smooth and transparent.

One of the films was mounted inside of an aluminum sample chamber that was then evacuated. The chamber consisted of 3 optical flats to allow absorption and emission data acquisition, and had a valve assembly for controlling the pressure of ambient gases. This chamber allowed the lifetime and intensity of the emission to be monitored as functions of O$_2$ pressure. Measurements were made using the system 10 shown in FIG. 1.

The decay of phosphorescence intensity as a function of time at several oxygen pressures for this Pt(TFPP) in PVC film is shown in FIG. 2, wherein curves 1 to 10 are respectively for O$_2$ pressures of 1, 10, 50, 100, 200, 300, 400, 500, 600, and 730 torr. Plots of $\bar{k}/k_o$ and $\tau_o/\bar{\tau}$ for this Pt(TFPP) in PVC film as a function of O$_2$ pressure are shown in FIG. 3.

EXAMPLE 2

Pd(TFPP) in PVC

Pd(TFPP) was synthesized following the procedure described in *Inorg.Chem.* 19:386, 1980. 10 mg of Pd(TFPP) was then dissolved in a 25 ml aliquot of the PVC stock solution described in Example 1. Films of Pd(TFPP) in PVC were made as in Example 1. Phosphorescence emission intensity decay curves, I(t), of the Pd(TFPP) in plasticized PVC film were determined at various molecular oxygen pressures ranging from 1 to 600 torr. Stern-Volmer plots of $\bar{k}/k_o$ and $\tau_o/\bar{\tau}$ were also made for this Pd(TFPP) in PVC film as a function of oxygen pressure. The data are shown in Table 3.

TABLE 3

| Data analysis of PdTFPP in PLS/PVC[a,b,c] | | | | | | | | |
|---|---|---|---|---|---|---|---|---|
| pO$_2$ | A$_1$ | k$_1$ | A$_2$ | k$_2$ | $\bar{k}$ | $\bar{\tau}$ | $\bar{k}/k_o$ | $\tau_o/\bar{\tau}$ |
| 1 | 0.91 | 1.05 | 0.09 | 0.79 | 1.02 | 984 | .1 | 1 |
| 10 | 0.80 | 1.34 | 0.20 | 2.92 | 1.65 | 669 | 1.61 | 1.47 |
| 50 | 0.37 | 2.02 | 0.63 | 5.56 | 4.25 | 295.5 | 4.16 | 3.33 |
| 100 | 0.32 | 2.92 | 0.68 | 9.43 | 7.35 | 182 | 7.18 | 5.41 |
| 200 | 0.26 | 3.73 | 0.74 | 14.08 | 11.34 | 123 | 11.1 | 8.0 |
| 300 | 0.30 | 4.89 | 0.70 | 18.52 | 14.4 | 98 | 14.1 | 10.0 |
| 500 | 0.15 | 5.24 | 0.85 | 19.61 | 17.4 | 72 | 17.2 | 13.7 |

[a]PLS/PVC = plasticized polyvinyl chloride as described above.
[b]Data taken by system 10.
[c]The k's are in (ms)$^{-1}$, and $\bar{\tau}$ is in $\mu$s.

EXAMPLE 3

Alternate matrices and the effect of plasticizer

Other polymer matrices such as polymethyl methacrylate (PMM), cellulose acetate (CA), and silicone polymer can be used as matrices for the Pt(TFPP), Pd(TFPP), or other luminescent aromatic molecule. In fact, these polymers are more permeable to gases than PVC and so can be used without plasticizer. For example, films of these matrices were made as described above from the following stock solutions that each contained 10 mg of Pt(TFPP):

PMM—1 g of polymethyl methacrylate (Aldrich) and 20 ml of tetrahydrofuran;

CA—1 g of cellulose acetate (Aldrich) and 20 ml of acetone; and,

PMB—1 g of dimethylsiloxane-bisphenol A-polycarbonate block copolymer (Petrarch Systems, Inc.) and 20 ml of tetrahydrofuran.

Figure 11:
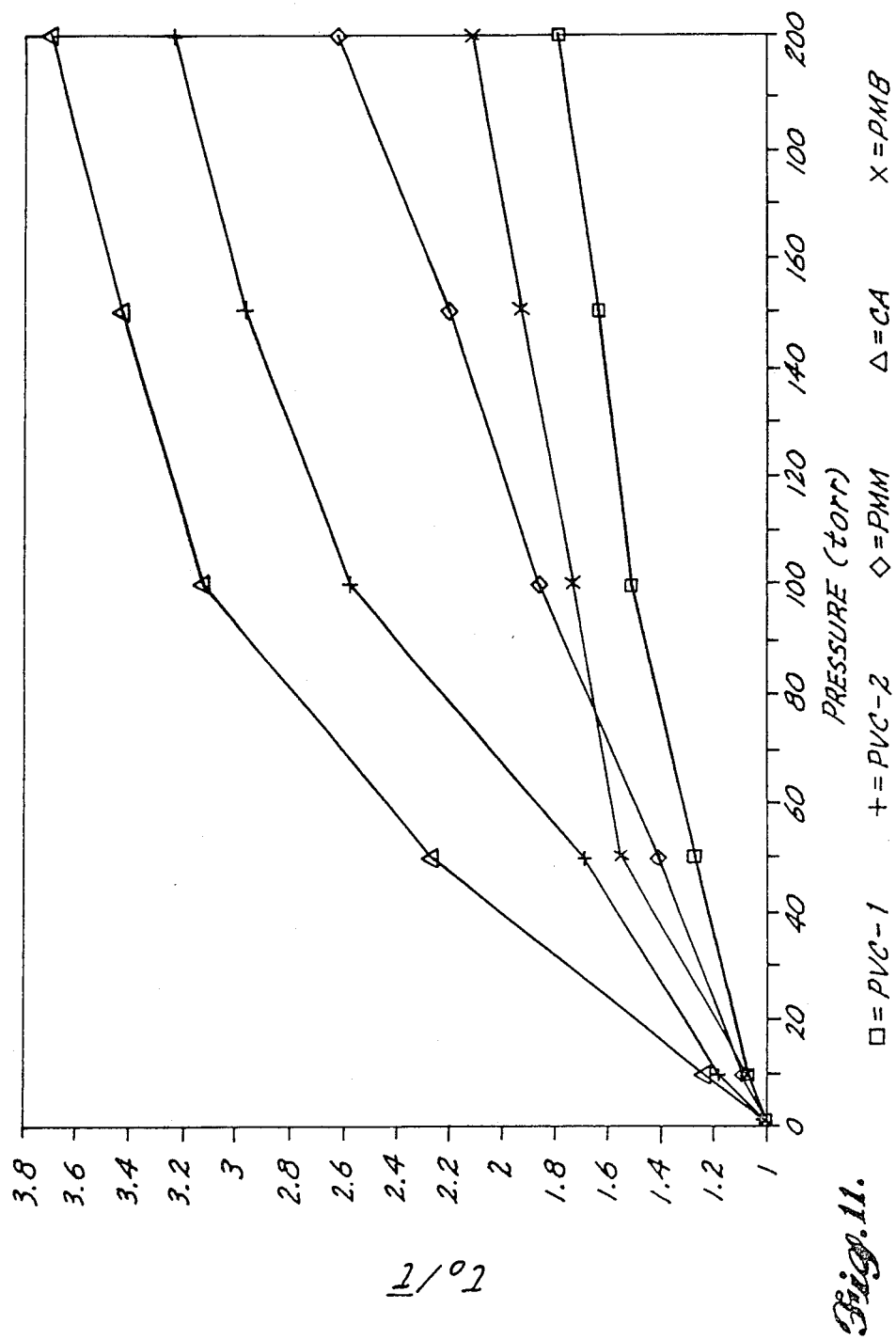
FIG. 11 presents Stern-Volmer plots for Pt(TFPP) in various film matrices containing various amounts of plasticizer, as described in Example 3; and, FIG. 12 presents Stern-Volmer plots of $\bar{k}/k_o$ for films containing various mixtures of Pt(TFPP) and Pd(TFPP), as described in Example 4.

Quenching plots of the Pt(TFPP) in PMM, CA, and silicone PMB films as a function of $O_2$ pressure are shown in FIG. 11.

FIG. 11 also shows data from two PVC films with different amounts of plasticizer, thus indicating the influence of plasticizer concentration on oxygen quenching. These films were made as described in Example 1: PVC-1 was made using 200 microliters of the plasticizer 2-nitrophenyloctaethylether, and PVC-2 was made using 500 microliters of the plasticizer.

EXAMPLE 4

Pt(TFPP) and Pd(TFPP) mixture in PVC

Figure 12:
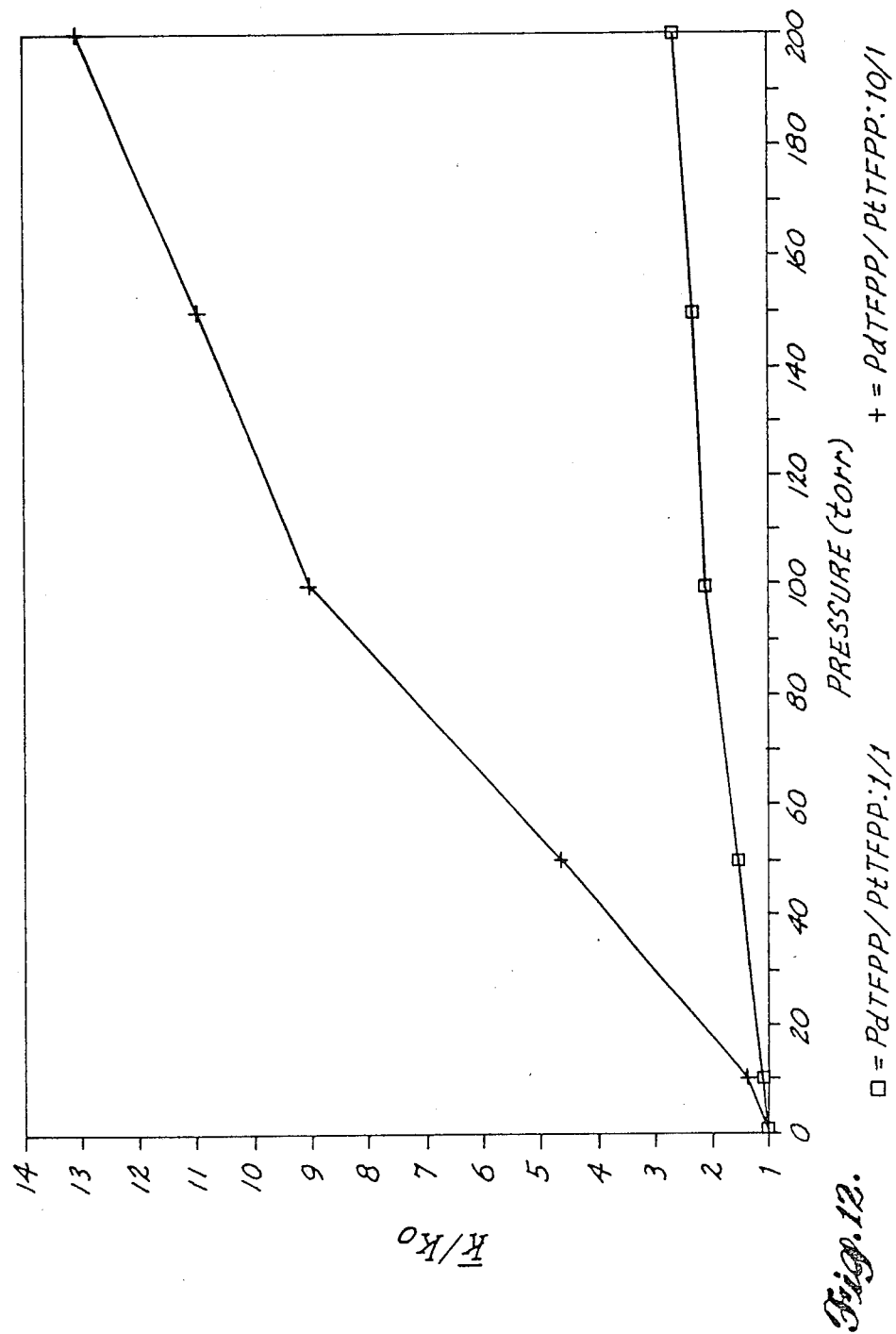

Films of Pt(TFPP) and Pd(TFPP) mixture with different ratios of the phosphorescent species were made from the PVC stock solution described in Example 1. Quenching plots as functions of $O_2$ pressure are shown in FIG. 12 for two plasticized PVC films with 10:1 and 1:1 ratios of the Pd:Pt mixture. Oxygen pressure sensitivity range can be adjusted by changing the concentration ratios of Pt(TFPP) and Pd(TFPP).

EXAMPLE 5

Light sensitivity studies

The stability of various oxygen quenching-sensitive compositions under extended illumination was determined. Various metalloporphyrins were cast in polymer films and then exposed to extended illumination as follows: The light from a 200 watt reflection bulb was shined on the films after passing through a water container, the glass bottom of the water container, and the plastic of a transparent plastic stand. Air was blown over the films as well. The purpose of the water and the airstream was to make sure that the films were not subject to heat stress. Also, by using the tungsten lamp and passing the light through water and plastic any high energy ultraviolet radiation was attenuated. Short wave UV would not be present under the conditions of this setup.

Pd and Pt derivations of OEP and TPP were synthesized as described in *J.Mol.Spectroscopy* 35(3):359–375, 1970. Pd(TBP) and Pt(TBP) were synthesized as described in *J.Amer.Chem.Soc.* 104:6278–6283, 1982. Pt(TFPP) and Pd(TFPP) were synthesized as described in Examples 1 and 2 above. The various metalloporphyrins were individually cast into polymer films as described in Example 1.

The metalloporphyrins and films were prepared fresh for this test and were subjected to 15 hours of illumination in the above-described setup. Absorptions, emission intensities, and emission lifetimes were measured before and after the 15 hour illumination period. The results are summarized in Table 4.

Summary of survival after 15 hours of illumination.

| Compound | Absorption | Emission[a,b] | Lifetimes[c] |
|---|---|---|---|
| Pd(OEP) | gone | | |
| Pt(OEP) | gone | | |
| Pd(TBP) | gone | | |
| Pt(TBP) | gone | | |
| Pd(TFPP) | survives | 65% | 90–94% |
| Pt(TFPP) | survives | 80% | 92–100% |
| Pd(TPP) | survives | 65% | 62–83% |
| Pt(TPP) | survives | 20% | 58–63% |

[a] Average emission peak intensity ratios after/before exposure to illumination.
[b] Pd(OEP), Pt(OEP), Pd(TBP), Pt(TBP) showed no phosphorescence emission after exposure to illumination.
[c] k or τ with system 10.

The absorption spectrum is a minimal test for survival of the compound. If the spectrum is gone, the compound is gone. The absorption spectra of neither the OEP nor the TBP rings survived 15 hours of illumination.

The absorption spectra for Pd(TFPP), Pt(TFPP), Pd(TPP), and Pt(TPP) showed growth of an impurity with an absorption at approximately 600 nm. For both the TFPP and the TPP rings the impurity appeared slightly blue shifted from Pd to Pt (with the shift more marked for the TPP rings). This would suggest that the impurity somehow contains or is associated with the metal.

For the TPP films the amount of emission was much more extensively quenched than for the TFPP films. Since the test for $O_2$ pressure depends on emission intensities and lifetimes, it appears that the TFPP molecules are the only suitable rings with respect to survival of emission properties after extended illumination. Furthermore, the lifetimes of the TFPP molecules appear to be the most hardy test for the amount of $O_2$, in the sense of remaining constant after extended illumination.

EXAMPLE 6

Extended illumination of perylene dibutyrate.

Peterson in U.S. Pat. No. 4,476,870 and in *Anal.-Chem.* 56:62–67, 1984, describes an oxygen sensor based on the fluorescence quenching of perylene dibutyrate (PDB). The latter paper reports: "A 5-day test showed an average loss of sensitivity of 6.5% per day due to continuous exposure to the blue excitation light when connected to a fiber optic sensor." We prepared a sample of this same dye in PVC with plasticizer and subjected it to 15 hours of illumination in the setup of Example 5. We observed that the emission decreased about 30% over this time period. Given the very different geometries of illumination for a fiber optic sensor and that of our setup, it is difficult to know the relative light fluxes. However, it is not unreasonable to assume that we can take our observations of PDB deterioration to mean that our extended 15 hours of illumination is roughly equivalent to 5 days on a light pipe. Thus we contemplate that the emission lifetimes of the TFPP molecules provide a much more stable measure of oxygen pressure than the emission intensities of Peterson's fluorescent dye of choice. We further contemplate that PDB and other oxygen-quenchable fluorescent substances known in the art can be used with our disclosed methods, which provide measurements of oxygen quenching that are insensitive to photodeterioration of the luminescent substance during use.

The term "plastic" as used herein refers to a polymeric product of large molecular weight that can be shaped by flow, including principally at least one polymeric starting material and permissible amounts of plasticizer as described above.

While the present invention has been described in conjunction with a preferred embodiment and illustrative examples, one of ordinary skill after reading the foregoing specification will be able to effect various changes, substitutions of equivalents, and other alterations to the methods and compositions set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A method of measuring oxygen concentration in a fluid, comprising the steps of:
   (a) contacting a test fluid with a sensor composition comprising a luminescent substance, whose luminescent emission is sensitive to quenching by oxygen, admixed in an oxygen-permeable matrix, the sensor composition exhibiting a nonexponential luminescent emission when irradiated with light containing wavelengths strongly absorbed by the luminescent substance,
   (b) irradiating the sensor composition with light containing wavelengths strongly absorbed by the luminescent substance,
   (c) terminating the irradiation of step (b),
   (d) measuring the flux of luminescent light emitted by the sensor composition during at least two time intervals comprising at least one time interval subsequent to step (c),
   (e) comparing the flux values measured in step (d) to obtain a ratioing R value,
   (f) determining the oxygen concentration in the test fluid by comparing the ratioing R value obtained in step (e) with a similarly obtained ratioing R value for at least one reference fluid of known oxygen concentration.

2. The method of claim 1 wherein the at least two time intervals for flux measurement in step (d) substantially encompass the period of linear decay of luminescent emission by the sensor composition subsequent to step (c).

3. The method of claim 2 wherein the at least two time intervals subdivide the period of linear decay of luminescent emission by the sensor composition subsequent to step (c) into substantially equal time intervals.

4. The method of claim 2 wherein the at least two time intervals are two in number.

5. The method of claim 4 wherein the ratioing R value is given by:

$$R = (I_1 - I_2)/(I_1 + I_2)$$

where $I_1$ is the flux of luminescent emission by the sensor composition measured during a first time interval and $I_2$ is the flux of luminescent emission by the sensor composition measured during a second time interval.

6. The method of claim 1 wherein the at least two time intervals for flux measurement in step (d) substantially encompass the period of detectable luminescent emission by the sensor composition subsequent to step (c).

7. The method of claim 6 wherein at least one of the at least two time intervals substantially encompasses the period of linear decay of luminescent emission by the sensor composition subsequent to step (c).

8. The method of claim 6 wherein the ratioing R value is given by:

$$R = I_1/I_2$$

wherein $I_1$ is the flux of luminescent emission by the sensor composition measured during the period of linear decay of luminescent emission by the sensor composition subsequent to step (c) and $I_2$ is the flux of luminescent emission by the sensor composition measured during any remaining period of detectable luminescent emission by the sensor composition.

9. The method of claim 1 wherein step (b) takes place during at least one of the at least two time intervals for flux measurement.

10. The method of claim 9 wherein at least one first time interval substantially encompasses the period leading up to an emission intensity plateau by the sensor composition during step (b) and at least one second time interval substantially encompasses the period of detectable luminescent emission by the sensor composition subsequent to step (c).

11. The method of claim 10 wherein the ratioing R value is given by:

$$R = I_1/I_2$$

wherein $I_1$ is the flux of luminescent emission by the sensor composition measured during the at least one first time interval and $I_2$ is the flux of luminescent emission by the sensor composition measured during the at least one second time interval.

12. A method of measuring oxygen concentration in a fluid, comprising the steps of:
   (a) contacting a test fluid with a sensor composition comprising a phosphorescent substance, whose phosphorescent emission is sensitive to quenching by oxygen, admixed in an oxygen-permeable matrix, the sensor composition exhibiting a nonexponential phosphorescent emission when irradiated with light containing wavelengths strongly absorbed by the luminescent substance,
   (b) irradiating the sensor composition with light containing wavelengths strongly absorbed by the phosphorescent substance,
   (c) terminating the irradiation of step (b),
   (d) measuring the intensity of phosphorescent light emitted by the sensor composition at a plurality of times subsequent to step (c),
   (e) fitting the measured intensity values as follows:

$$I(t) = A_1 e^{-k_1 t} + A_2 e^{-k_2 t}$$

wherein I(t) is the measured intensity at time t, e is the exponential function, and $A_1$, $k_1$, $A_2$, and $k_2$ are fitting parameters, (f) determining the average decay rate of phosphorescent emission by the sensor composition, k, from the fitting parameters in step (e) as follows:

$$k=(A_1k_1+A_2k_2)/(A_1+A_2),$$

(g) determining the oxygen concentration in the test fluid by comparing the average decay rate determined in step (f) with a similarly obtained $\bar{k}$ value for at least one reference fluid of known oxygen concentration.

13. A method of measuring oxygen concentration in a fluid, comprising the steps of:
   (a) contacting a test fluid with a sensor composition comprising a phosphorescent substance, whose phosphorescent emission is sensitive to quenching by oxygen, admixed in an oxygen-permeable matrix, the sensor composition exhibiting a nonexponential phosphorescent emission when irradiated with light containing wavelengths strongly absorbed by the phosphorescent substance,
   (b) irradiating the sensor composition with light containing wavelengths strongly absorbed by the phosphorescent substance,
   (c) terminating the irradiation of step (b),
   (d) measuring the intensity of phosphorescent light emitted by the sensor composition at a plurality of times subsequent to step (c),
   (e) fitting the measured intensity values as follows:

$$I(t)=A_1e^{-k_1t}+A_2e^{-k_2t}$$

wherein I(t) is the measured intensity at time t, e is the exponential function, and $A_1$, $k_1$, $A_2$, and $k_2$ are fitting parameters,
   (f) determining the average decay time of phosphorescent emission by the sensor composition, $\bar{\tau}$, from the fitting parameters in step (e) as follows:

$$\bar{\tau}=(A_1k_1^{-1}+A_2k_2^{-1})/(A_1+A_2),$$

(g) determining the oxygen concentration in the test fluid by comparing the average decay time determined in step (f) with a similarly obtained $\bar{\tau}$ value for at least one reference fluid of known oxygen concentration.

14. A method of measuring oxygen concentration in a fluid, comprising the steps of:
   (a) contacting a test fluid with a sensor composition comprising a luminescent substance, whose luminescent emission is sensitive to quenching by oxygen, admixed in an oxygen-permeable matrix, the sensor composition exhibiting a nonexponential luminescent emission when irradiated with light containing wavelengths strongly absorbed by the luminescent substance,
   (b) irradiating the sensor composition with light containing wavelengths strongly absorbed by the luminescent substance,
   (c) terminating the irradiation of step (b),
   (d) measuring the intensity of luminescent light emitted by the sensor composition at a plurality of times subsequent to step (c),
   (e) from the measured intensities in step (d), determining the slope of emission decay during the period of linear decay of luminescent emission by the sensor composition,
   (f) determining the oxygen concentration in the test fluid by comparing the slope value obtained in step (e) with a similarly obtained slope value for at least one reference fluid of known oxygen concentration.

15. A method of measuring oxygen concentration in a fluid, comprising the steps of:
   (a) contacting a plurality of reference fluids of known oxygen concentration with a sensor composition comprising a luminescent substance, whose luminescent emission is sensitive to quenching by oxygen, admixed in an oxygen-permeable matrix, the sensor composition exhibiting a nonexponential luminescent emission when irradiated with light containing wavelengths strongly absorbed by the luminescent substance,
   (b) irradiating the sensor composition with light containing wavelengths strongly absorbed by the luminescent substance,
   (c) terminating the irradiation of step (b),
   (d) measuring the intensity of luminescent light emitted by the sensor composition during a plurality of times subsequent to step c),
   (e) from the measured intensities in step (d), determining the intensity versus time profile of emission decay for each reference fluid during the period of linear decay of luminescent emission by the sensor composition,
   (f) contacting a test fluid of unknown oxygen concentration with the sensor composition and repeating steps (b) and (c) with the test fluid,
   (g) measuring the time it takes for the intensity of luminescent light emitted by the sensor composition subsequent to step (f) to fall to a predetermined intensity value which can be referenced against the intensity versus time profiles determined in step (e), and
   (h) determining the oxygen concentration in the test fluid by comparing the time value measured in step (g) with the intensity versus time profiles determined in step (e) for the reference fluids of known oxygen concentrations.

16. A method of measuring oxygen concentration in a fluid, comprising the steps of:
   (a) contacting a plurality of reference fluids of known oxygen concentration with a sensor composition comprising a luminescent substance, whose luminescent emission is sensitive to quenching by oxygen, admixed in an oxygen-permeable matrix, the sensor composition exhibiting a nonexponential luminescent emission when irradiated with light containing wavelengths strongly absorbed by the luminescent substance,
   (b) irradiating the sensor composition with light containing wavelengths strongly absorbed by the luminescent substance,
   (c) terminating the irradiation of step (b),
   (d) measuring the intensity of luminescent light emitted by the sensor composition during a plurality of times subsequent to step (c),
   (e) from the measured intensities in step (d), determining the intensity versus time profile of emission decay of each reference fluid during the period of linear decay of luminescent emission by the sensor composition, (f) contacting a test fluid of unknown oxygen concentration with the sensor composition and repeating steps (b) and (c) with the test fluid, (g) measuring the intensity of luminescent light emitted by the sensor composition at a given time interval subsequent to step (f), which time interval falls within the period of linear decay for the sensor composition, and (h) determining the oxygen concentration in the test fluid by comparing the intensity value measured in step (g) with the intensity versus time profiles determined in step (e) for the reference fluids of known oxygen concentrations.

17. The method of claims 1, 12, 13, 14, 15, or 16 wherein the test fluid is blood.

18. The method of claims 1, 12, or 13 wherein the test fluid is blood and the at least one reference fluid is air.

19. The method of claims 1, 12, 13, 14, 15, or 16 wherein the irradiating light and emitted light are transmitted by fiber optic means.

20. The method of claim 19 wherein the sensor composition is positioned in a light path of a single optical fiber.

21. The method of claims 1, 14, 15, or 16 wherein the luminescent substance is selected from the group consisting of phosphorescent and fluorescent substances.

22. The method of claim 21 wherein the luminescent substance is a metallo derivative of a porphyrin, chlorin, bacteriochlorin, or isobacteriochlorin.

23. The method of claim 22 wherein the luminescent substance is octaethylporphyrin, tetraphenylporphyrin, tetra(pentafluorophenyl)porphyrin, tetrabenzporphyrin, or the chlorins, bacteriochlorins, or isobacteriochlorins of said porphyrins.

24. The method of claim 22 wherein the luminescent substance is a platinum or palladium derivative of a porphyrin, chlorin, bacteriochlorin, or isobacteriochlorin.

25. The method of claim 21 wherein the luminescent substance is partially or wholly fluorine substituted.

26. The method of claims 1, 14, 15, or 16 wherein the luminescent substance comprises one or both of a platinum derivative and a palladium derivative of a tetra(pentafluorophenyl)porphyrin.

27. The method of claims 1, 12, 13, 14, 15 or 16 wherein the oxygen-permeable matrix is a plastic.

28. The method of claim 27 wherein the plastic comprises one or more of polyvinyl chloride, polymethyl metacrylate, cellulose acetate, and silicon-polybicarbonate copolymer, with or without a plasticizer.

29. The method of claim 12 or 13 wherein the phosphorescent substance is a metallo derivative of a porphyrin, chlorin, bacteriochlorin, or isobacteriochlorin.

30. The method of claim 29 wherein the phosphorescent substance is octaethylporphyrin, tetraphenylporphyrin, tetra(pentafluorophenyl)porphyrin, tetrabenzporphyrin, or the chlorins, bacteriochlorins, or isobacteriochlorins of said porphyrins.

31. The method of claim 29 wherein the phosphorescent substance is a platinum or palladium derivative of a porphyrin, chlorin, bacteriochlorin, or isobacteriochlorin.

32. The method of claim 29 wherein the phosphorescent substance is partially or wholly fluorine substituted.

33. The method of claim 12 or 13 wherein the phosphorescent substance comprises one or both of a platinum derivative and a palladium derivative of a tetra(pentafluorophenyl)porphyrin.

* * * * *

UNITED STATES PATENT AND TRADEMARK OFFICE
CERTIFICATE OF CORRECTION

PATENT NO. : 4,810,655                                  Page 1 of 2
DATED      : March 7, 1989
INVENTOR(S): Khalil et al.

It is certified that error appears in the above-identified patent and that said Letters Patent is hereby corrected as shown below:

Column 2, line 20: "5us" is changed to --5µs-- line 37: "50us" is changed to --50µs-- lines 65 & 66: "octaephylporphyrin" is changed to --octaethylporphyrin--

Column 3, line 13: "$\tau_0/\tau$" is changed to --$\overline{\tau_0/\tau}$--

Column 4, line 34: after "∅" insert --is

Column 6, line 50: "active" is changed to --activate--

Column 7, line 7: "e" is changed to --be-- line 27: "0.31" is changed to --0.37-- line 50: "in" is changed to --In--

Column 9, line 13: "specically" is changed to --specially--

Column 12, lines 40 & 41: "prophyrins" is changed to --porphyrins-- line 67: "photooxidation" is changed to --photo-oxidation--

Column 13, lines 59 & 60: "molecules" is changed to --molecule--

Column 13, line 64 and Column 14, line 1, before "-continued" insert -- TABLE 2 --.

Column 13, line 67: "$E_{1/2}^{ox}$" is changed to --$E_{1/2}^{ox}$-- line 68: "85.140" is changed to --95:140--

Column 14, line 3: "$E_{1/2}^{ox}$" is changed to --$E_{1/2}^{ox}$--

Column 15, line 53: "$H_2$(TEPP)" is changed to --$H_2$(TFPP)--

Column 16, line 53: "Alternate" is changed to --Alternative--

UNITED STATES PATENT AND TRADEMARK OFFICE
CERTIFICATE OF CORRECTION

PATENT NO. : 4,810,655
DATED : March 7, 1989
INVENTOR(S) : Khalil et al.

It is certified that error appears in the above-identified patent and that said Letters Patent is hereby corrected as shown below:

Column 21, line 47: "$\tau$" is changed to --$\bar{\tau}$--

Column 22, line 26: "c)" is changed to --(c)--

Signed and Sealed this

Thirteenth Day of February, 1990

*Attest:*

JEFFREY M. SAMUELS

*Attesting Officer*     *Acting Commissioner of Patents and Trademarks*